United States Patent [19]

Esrock

[11] Patent Number: 6,113,391
[45] Date of Patent: *Sep. 5, 2000

[54] DISPOSABLE DENTAL SYRINGE TIP

[76] Inventor: Bernard S. Esrock, 320 Dungate Dr., Chesterfield, Mo. 63017

[ * ] Notice: This patent is subject to a terminal disclaimer.

[21] Appl. No.: 09/018,585

[22] Filed: Feb. 4, 1998

Related U.S. Application Data

[63] Continuation of application No. 08/423,994, Apr. 18, 1995, Pat. No. 5,772,433.

[51] Int. Cl.$^7$ ..................................................... A61G 17/02
[52] U.S. Cl. .................................. 433/80; 433/85; 433/88
[58] Field of Search .................................... 433/80, 88, 89, 433/81, 84, 85, 100, 215; 601/162; 604/80

[56] References Cited

U.S. PATENT DOCUMENTS

| | | | |
|---|---|---|---|
| D. 352,354 | 11/1994 | Davis et al. | D24/112 |
| 1,940,210 | 12/1933 | Frederick . | |
| 2,117,622 | 5/1938 | Morton et al. . | |
| 2,199,844 | 5/1940 | Tucker . | |
| 2,531,793 | 11/1950 | Sulek . | |
| 2,550,565 | 4/1951 | Hyser | 433/88 |
| 3,254,646 | 6/1966 | Staunt et al. . | |
| 3,375,823 | 4/1968 | Pamplin et al. . | |
| 3,391,696 | 7/1968 | Woodward . | |
| 3,401,691 | 9/1968 | Beu . | |
| 3,527,219 | 9/1970 | Greenberg . | |
| 3,570,483 | 3/1971 | Stram . | |
| 3,593,423 | 7/1971 | Jones et al. . | |
| 3,698,088 | 10/1972 | Austin, Jr. . | |
| 3,847,150 | 11/1974 | Scheuermann . | |
| 3,874,083 | 4/1975 | Buckley . | |
| 3,965,577 | 6/1976 | Wegner . | |
| 3,968,796 | 7/1976 | Baker . | |
| 4,026,025 | 5/1977 | Hunt . | |
| 4,149,315 | 4/1979 | Page, Jr. et al. . | |
| 4,249,899 | 2/1981 | Davis | 433/32 |
| 4,676,749 | 6/1987 | Mabille | 433/88 |
| 4,907,968 | 3/1990 | Eisner et al. | 433/80 |
| 4,975,054 | 12/1990 | Esrock | 433/80 |
| 4,984,984 | 1/1991 | Esrock | 433/88 |
| 5,049,071 | 9/1991 | Davis et al. | 433/80 |
| 5,192,206 | 3/1993 | Davis et al. | 433/80 |
| 5,236,356 | 8/1993 | Davis et al. | 433/80 |
| 5,242,300 | 9/1993 | Esrock | 433/80 |
| 5,306,146 | 4/1994 | Davis et al. | 433/80 |
| 5,326,685 | 7/1994 | Gaglio et al. | 433/215 |
| 5,342,195 | 8/1994 | Davis et al. | 433/80 |
| 5,460,619 | 10/1995 | Esrock | 433/80 |
| 5,474,450 | 12/1995 | Chronister | 433/80 |
| 5,489,205 | 2/1996 | Davis et al. | 433/80 |
| 5,591,389 | 1/1997 | Esrock | 264/171.12 |

FOREIGN PATENT DOCUMENTS 3322716   1/1985   Germany .

*Primary Examiner*—Nicholas D. Lucchesi
*Attorney, Agent, or Firm*—Senniger, Powers, Leavitt & Roedel

[57] ABSTRACT

A dental syringe tip for use with a hand-piece of an air-water syringe to deliver air and water to a mouth of patient. The syringe has air and water conduits for delivering air and water to a discharge end of the hand-piece. The dental syringe tip includes a single unitary tube releasably engageable with the discharge end of the hand-piece. The tube has a fluid passageway extending from an intake port at an intake end of the tube for fluid communication with the air and water conduits of the hand-piece. In addition, the tube has a discharge port at a discharge end of the tube for delivering at least one of the air and water through the passageway to the mouth of the patient. The intake end of the tube is shaped and constructed to enable air and water flow through the air and water conduits when at least a portion of the intake end of the tube engages the discharge end of the hand-piece. The intake end of the tube at least partially defines a chamber when the portion of the intake end of the tube engages the discharge end of the hand-piece for transporting air from the air conduit of the hand-piece to the intake port of the tube and for transporting water from the water conduit of the hand-piece to the intake port.

9 Claims, 1 Drawing Sheet

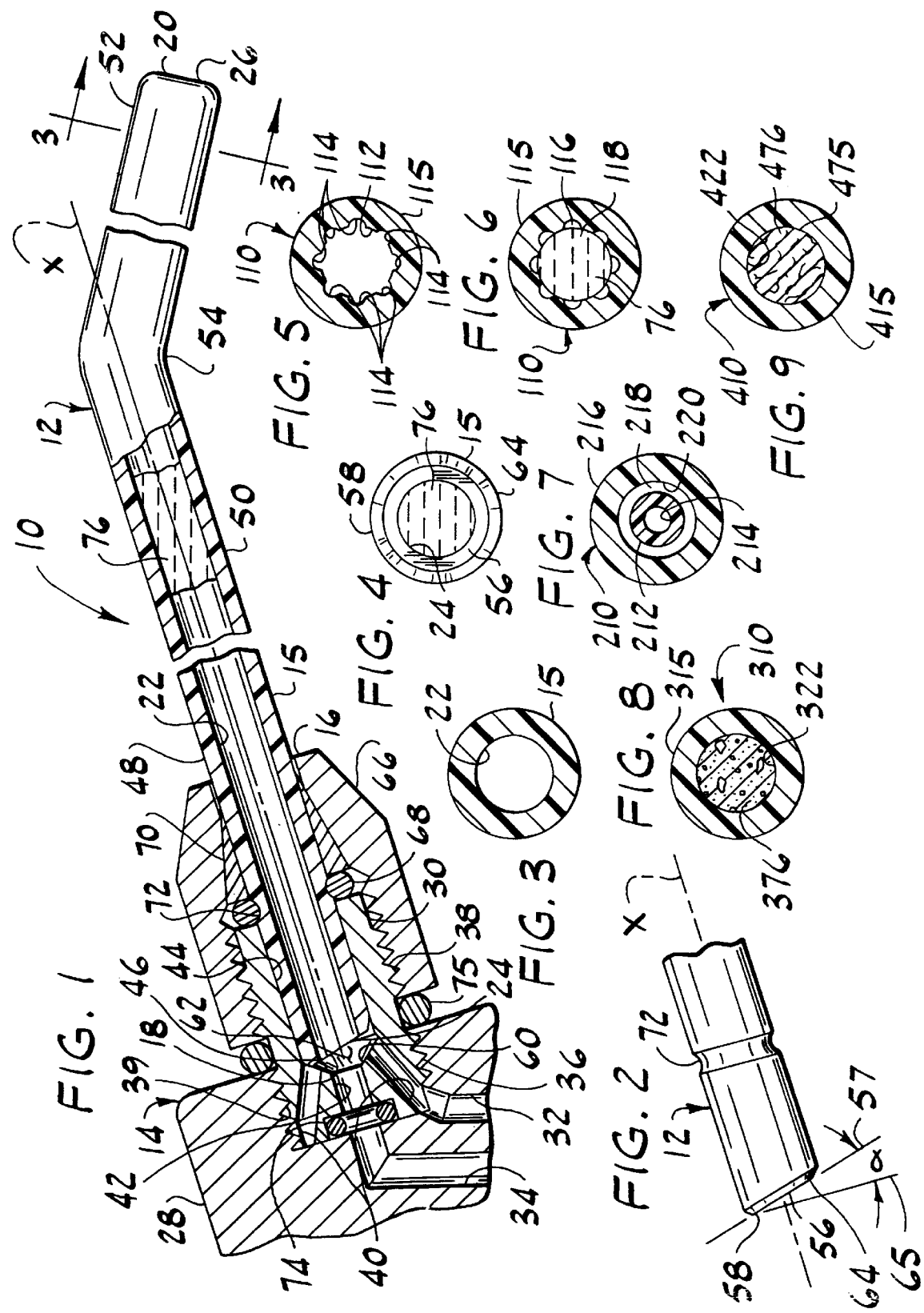

DISPOSABLE DENTAL SYRINGE TIP

This application is a continuation of U.S. patent application Ser. No. 08/423,994, filed Apr. 18, 1995 now U.S. Pat. No. 5,772,433 hereby incorporated by reference.

This invention relates to air-water syringes, and more particularly to syringe tips for dental syringes.

Air-water syringes are used by dentists and dental technicians for many dental procedures, such as cleaning debris from a patient's teeth and mouth. The teeth and mouth are cleaned by the spraying of a stream of water or a stream of air from the syringe. A typical air-water syringe has a hand-piece and a syringe tip releasably attached to the hand-piece.

Many dentists use disposable (single use only) syringe tips to avoid spreading infectious diseases from one patient to another. A typical disposable air-water syringe tip has inner and outer coaxial tubes which define discrete air and water passageways. The water passageway is defined by the inner surface of the inner tube. The air passageway is defined by the outer surface of the inner tube and the inner surface or the cuter tube. Water is directed from a water passageway in the hand-piece to the patient via the water passageway in the tip. Air is directed from an air passageway in the hand-piece to the patient via the air passageway in the tip.

A disadvantage of such syringe tips is the cost to manufacture. These disposable syringe tips are viewed as too expensive by many dentists since a tip is to be discarded after a single use. These dentists find it more cost effective to purchase autoclavable (i.e., reusable) syringe tips. An autoclavable syringe tip is generally much more expensive than a disposable syringe tip, but may be used repeatedly if it is sterilized between uses.

During a dental procedure it may be desirable to have the patient rinse with a mouthwash or other type of solution. Dispensing the rinse in a manner separate from the air-water syringe can be inconvenient and time consuming.

An attempt to simply delivery of a rinse as described in U.S. Pat. No. 3,593,423, is to attach the air-water syringe to a source of the rinse and selectively spray it into a patient's mouth. Drawbacks to this approach are the need for special air-water syringes, the inability to easier select from various different types of rinses and the need to periodically fill the rinse container.

SUMMARY OF THE INVENTION

Among the several objects of this invention may be noted the provision of an improved syringe-tip for a dental tool; the provision of such a syringe tip that has a pre-measured amount of liquid such as a rinse or mouthwash; the provision of such a syringe tip that can function as an air-water syringe tip immediately after injecting the rinse or mouthwash into a patient's mouth; the provision of such a syringe tip which is of relatively simple and inexpensive construction; and the provision of such a syringe tip which is disposable.

Generally, a syringe tip of this invention is used with a hand-piece of an air-water syringe. The hand piece comprises air and water conduits for delivering air and water to a discharge end of the hand-piece. The dental syringe tip is releasably engageable with the discharge end of the hand-piece and comprises a single unitary tube having an intake end and a discharge end. The tube defines a fluid passageway having an intake port for fluid communication with the air and water conduits of the hand-piece and a discharge port for pressurized delivery of the air and water to the mouth of a patient. The intake end of the tube is shaped and constructed to avoid blockage of the air and water conduits by the tube when a portion of the intake end of the tube engages the discharge end of the hand-piece. A chamber is defined at least in part by the intake end of the tube and the portion of the hand-piece when the portion of the intake end of the tube engages the discharge end of the hand-piece. The chamber provides fluid communication between the air conduit of the hand-piece and intake port and provides fluid communication between the water conduit of the hand-piece and the intake port so that air and water flow-na through the air and water conduits flows through the passageway of the syringe tip via the channel.

In another aspect of the present invention, a syringe tip comprises a tube releasably engageable with the discharge end of a hand-piece. The tube has an intake end and a discharge end. A fluid passageway is defined at least in part by the tube and has an intake port and a discharge port. The intake port is adjacent the intake end of the tube for fluid communication with the fluid conduit of the hand-piece. The discharge port is adjacent the discharge end of the tube for pressurized delivery of the fluid to the mouth of a patient. A viscous liquid is within and occludes the fluid passageway. The liquid is adapted to be discharged from the discharge port into the mouth of the patient when the fluid is delivered to the mouth of the patient via the hand-piece and fluid passageway.

Other objects and features will be in part apparent and in part pointed out hereinafter.

BRIEF DESCRIPTION OF THE DRAWINGS

FIG. 1 is a side elevational view of a syringe tip of the present invention inserted into a hand-piece of a dental syringe with portions broken away to show detail;

FIG. 2 is a fragmented side elevational view so the syringe tip of FIG. 1 showing a forward portion of the syringe tip;

FIG. 3 is cross sectional view taken along the plane of line 3—3 of FIG. 1;

FIG. 4 is an end view of the syringe tip of FIG. 2 showing the inlet end of the syringe tip;

FIG. 5 is a cross sectional view of another syringe tip of the present invention having a fluted inner surface;

FIG. 6 is a cross sectional view OL the syringe tip of FIG. 5 showing a viscous liquid within the tip;

FIG. 7 is a cross sectional view of another syringe tip of the present invention having an air passageway coaxial with the water passageway;

FIG. 8 is a cross sectional view of another syringe tip of the present invention similar to the syringe tip of FIGS. 1–4, but having a treating agent in the form of a foam within the fluid passageway of the syringe tip; and FIG. 9 is a cross section view of another syringe tip of the present invention similar to the syringe tip of FIG. 8, but having a body of porous material within the fluid passageway for holding a treating agent.

Corresponding reference characters indicate corresponding parts throughout the several views of the drawings.

DETAILED DESCRIPTION OF THE PREFERRED EMBODIMENT

An air-water dental syringe of the present invention is indicated generally at 10 in FIG. 1. The dental syringe delivers air and water to the mouth of a patient and comprises a syringe tip generally indicated at 12 and a hand-piece generally indicated at 14.

Preferably, the syringe tip 12 is disposable, i.e., intended for a single use. It is releasably engageable with a discharge end 16 of the hand-piece. The syringe tip 12 (described in greater detail below) comprises a single unitary tube 15 having an intake end 18 and a discharge end 20. The tube defines a fluid passageway 22 having an intake port 24 at the intake end 18 of the tube and a discharge port 26 at the discharge end of the tube.

The hand-piece 14 includes a handle portion 28 and a stem 30 extending from a discharge end of the handle portion. The handle portion 28 has a first fluid conduit 32 (air conduit for directing an air stream to the fluid passageway 22 and a second fluid conduit 34 (water conduit) for directing a water stream to the fluid passageway. The stem 30 has first and second external screw threads 36, 38, air passages 40, a central water passage 42, and a socket 44. The first screw thread 36 mates with a threaded bore 39 in the handle portion 28 to secure the stem 30 to the handle portion. With the stem 30 inserted into the handle portion 28, the central water passage 42 aligns with and is in fluid communication with the water conduit 34 of the handle position 28, and the air passages 40 communicate with the air conduit 32 of the handle portion. Water discharged from the water conduit 34 flows through the central water passage 42 and into an inner end 46 of the socket 44 (the left most end of the socket as viewed in FIG. 1). Air discharged from the air conduit 32 flows through the air passages 40 and into the inner end 46 of the socket 44. As described in greater detail below, the socket 44 is sized and shaped for receiving the intake end 18 of the tip.

The tube 15 has a rear portion 48, an intermediate portion 50 and a forward portion 52. The rear portion 48 extends forward along an axis X from the intake end 18 of the tube to the intermediate portion 50 and the forward portion 52 extends generally forward from the intermediate portion to the discharge end 20. Preferably, the intermediate portion 50 of the tube has a bend 54.

The intake end 18 of the tube 15 has an intake end face 56 (FIG. 4) circumscribing and defining the intake port 24. The intake end face 56 (FIG. 4) of the tube is asymmetrical to the axis X, and preferably is generally planar and lies in a plane 57 oblique to the axis (see FIG. 2). In other words, the plane 57 of the intake end face 56 is slanted (i.e., raked) at an angle α from perpendicular. Preferably, the angle α is at least approximately 1°. The intake end 18 has a rearward-most portion 58 (i.e., the left-most portion of the tip as viewed in FIG. 2). Because of the slant of the intake end face, the rearward-most portion 58 of the intake end 18 is axially rearward of the entire intake port 24.

As discussed above, the socket 44 of the stem is sized and shaped for receiving the rear portion 48 of the tube 15. When the syringe tip 12 is in the socket, air or water flowing into the socket via either conduit 32, 34 flows through the tube. Preferably, when the syringe tip 12 is fully inserted into the socket 44 (see FIG. 1), the rearward-most portion 58 of the intake end 18 engages a beveled inner surface 60 of the stem (i.e., the surface defining the inner end of the socket). With the syringe tip 12 so positioned, the intake end face 56 of the syringe tip and the beveled inner surface 60 of the stem define a chamber 62. The chamber 62 provides fluid communication between the air conduit 32 of the hand-piece 14 and the intake port 24 so that air flowing through the air conduit flows through the passageway 22 of the syringe tip via the chamber. The chamber 62 also provides fluid communication between the water conduit 34 of the hand-piece 14 and the intake port 24 so that water flowing through the water conduit 34 flows through the passageway 22 of the syringe tip via the chamber 62. Because of the slanted angle α of the intake end face 56, a forward portion 64 of the intake end face (i.e., the lower-most portion of the intake end face as viewed in FIGS. 2 and 4) is spaced from the beveled inner surface 60 of the stem 30 when the rearward-most portion 58 engages the beveled inner surface. In other words, the slant of the intake end face 56 maintains a spacing between the forward portion 64 of the intake end face and the beveled inner surface 60. Also, the forward portion 64 of the intake end face 56 is spaced axially forward of a plane (designated at 65 in FIG. 2) which is perpendicular to the axis X and intersects the rearward-most portion 58 of the intake end. This spacing maintains the chamber 62 and avoids blockage of the air and water conduits 32, 34 by the tube 15 when the tip if fully inserted in the socket 44 (i.e., when the rearward-most portion 58 of the intake end 18 engages the beveled inner surface 60). In other words, maintaining the chamber 62 prevents the intake end 18 of the tip from sealing against the beveled inner surface 60 and stopping flow from the conduits 32, 34 to the fluid passageway 22.

Although the intake end face 56 is preferably planar id and oblique to axis X, it is to be understood that the intake end face may be some other shape or configuration to prevent seating. For example, an intake end face of the present invention could instead have one or more notches which prevent at least a portion of such face from contacting the wall.

The tip 12 is releasably secured to the stem 30 by a nut 66 threadable onto the second external threads 38 of the stem. An O-ring 68 is positioned over the syringe tip 12 and abuts an end of the stem 30 to prevent leakage of the air stream. The nut 66 urges a generally conical shaped sleeve 70 against the O-ring to hold the O-ring in place. Preferably, the tip 12 includes a circumferential groove 72 around its periphery and spaced axially forward of its intake end 18 to receive the O-ring 68. Preferably, the engagement of the groove 72 by the O-ring 68 retains the tip 12 in the socket 44 when the tip 12 is in its fully inserted position. Also preferably, the tip 12 may be inserted into and removed from the stem 30 without loosening the nut 66. Moreover, the intake end 18 of the tube 15 is preferably chamfered or rounded so that as the tip is inserted into the stem 30, the chamfered intake end 18 acts to force the O-ring 68 radially outwardly and the syringe tip 12 is pushed through the O-ring 68 until the O-ring aligns with and is seated in the groove 72. A second O-ring 74 is located in a recess in the stem 30 and surrounds the water passage 42 to prevent leakage of water between the handle portion 28 and stem. A third O-ring 75 is squeezed between the stem 30 and handle portion 28 to prevent external leakage of air from the hand-piece 14.

Preferably, the syringe tip 12 is made by extrusion of a stiff medical grade polyvinyl chloride or any ocher suitable synthetic resin having a durometer hardness reading of least approximately 60 Shore D (most preferably 81 Shore D) and a flex modulus of at least approximately 10,000 psi (most preferably 12,000 psi). The ends of the tube 15 are then chamfered and the tube is bent into its final shape.

As shown in FIG. 4, the tube 15 may contain treating agent in the form of a viscous liquid 76 within and occluding the fluid passageway 22. Pressurized air or water flowing from the hand-piece 14 through the fluid Passageway 22 in the tip pushes the liquid 76 through the fluid passageway, out of the discharge port 26 and into the mouth of the patient. After the liquid 76 is discharged from the fluid passageway 22, the syringe tip 12 operates as a conventional syringe tip.

Preferably, the liquid 76 is a concentrated mouthwash gel, such as MORGAN & BERRY®mouthwash gel, commercially available from Perio of Dublin, Ohio. Other treating agents such as mouthwash, numbing agents, softening agents, antiseptics, colorings, medications, etc., may also be used. Also, the treating agent may alternatively be solid or semisolid.

Preferably, the viscous liquid 76 has a viscosity which is sufficiently great to resist seepage out of the fluid passageway 22 before engagement of the tube 15 with the hand-piece 14 and before delivery of the liquid through the fluid passageway. To this end, the surface of the viscous liquid 76 is preferably adapted to congeal (e.g., form a protective skin) when exposed to air. Formation of a protective skin occurs due to hydration of the exposed surface and prevents leakage of the liquid from the tip 12 during shipping or transportation of the tip.

The viscous liquid 76 is preferably contained within the intermediate portion 50 of the tube and upstream from the bend 54. The bend 54 forms a slight restriction, i.e., reduction of diameter (not shown) of the fluid passageway 22 adjacent the bend. In the event the liquid 76 undesirably dries to form a solid plug, the restriction prevents forward movement of the plug within the passageway 22. Preferably, the amount of liquid 76 contained in the tip is approximately 0.1 cm$^3$ of liquid.

In operation, the disposable syringe tip 12 is fully inserted into the socket 44 of the hand-piece 14 so that the rearward-most portion 58 of the tube engages the beveled inner surface 60 of the stem and so that the O-ring 68 seats in the circumferential groove 72. An air or water button (not shown) is then depressed to force air or water from its respective conduit in the hand-piece 14, into the chamber 62, and through the fluid passageway 22 of the syringe tip 12. The air or water forces (carries) the liquid 76 out of the fluid passageway and into the mouth of a patient. After the liquid 76 is discharged from the passageway 22, the syringe tip 12 operates as a conventional dental syringe tip. When the dental procedure has been completed, the syringe tip 12 is discarded.

Another syringe tip of the present invention is indicated generally at 110 in FIG. 5. The syringe tip 110 is similar to the syringe tip 10, but includes a fluted surface 112 having a plurality of generally parallel flutes 114 extending the length of the tube 115. As shown in FIG. 6, the fluted tip may also contain a pre-measured quantity of liquid 76. The flutes 114 and viscous liquid 76 define a plurality of elongate air passageways 116 circumferentially spaced about the elongate fluid passageway 118 and extending the length of the syringe tip, 110. Surface tension of the liquid 76 prevents the liquid from flowing into and occluding the air passageways 116. Pressurized air passing through the tip flows through the air passageways 116 and around the liquid 76 without pushing the liquid through the discharge port 26. Preferably, the liquid 76 is discharged from the tube 115 only by delivery of water through the fluid passageway 118. Thus, a dentist may use the syringe as an air syringe without discharging the liquid 76, and then discharge the liquid by injecting water from the hand-piece 14 through the fluid passageway 118.

A third embodiment of the syringe tip is indicated generally at 210 in FIG. 7. The tube has an inner tube 212 and an outer tube 216. The inner surface of the inner tube defines a first fluid (or water) passageway 214. The outer tube 216 is generally coaxial with and surrounds the inner tube 212. The outer tube 216 is radially spaced from the inner tube 212 to create an annulus 218 between the inner and outer tubes extending the length of the tip. This annulus constitutes a second fluid (or air) passageway 220. The bend 54 of the tip is sufficient to hold the two tubes together without the need for bonding or joining. Preferably, a viscous liquid 76 (not shown) is within the first passageway 214 of the tip for delivery into the mouth of a patient.

A fourth syringe tip of the present invention is generally indicated at 310 in FIG. 8. The syringe tip 310 is similar to the syringe tip of FIGS. 1–4 except the treating agent is in the form of a foam 376. Preferably, a lengthwise portion of tube 315 is generally filled with foam 376. Preferably, the foam is water soluble and adapted to dissolve in water passing through passageway 322.

A fifth syringe tip of the present invention is generally indicated at 410 in FIG. 9. The syringe zip 410 is similar to syringe tip 310 except the syringe tip 410 includes a body of porous material 475 (treating agent carrier) for holding a treating agent 476, which may be liquid, semisolid or solid (e.g., granular). The body of porous material 475 may comprise a wad of cotton and may be soaked (or otherwise filled) with the treating agent prior to insertion into the tube 415, or the porous material may absorb the treating agent after placement of the porous material into the passageway 422. The body 475 is contained by the tube 415 so that water passing through the passageway 422 washes the treating agent from the body and carries the treating agent out the discharge port (not shown). Preferably, the body is disposed within the intermediate portion of the tube upstream from the bend to prevent the body from being discharged from the tube.

In view of the above, it will be seen that the several objects of the invention are achieved and other advantageous results attained.

As various changes could be made in the above constructions without departing from the scope of the invention, it is intended that all matter contained in the above description or shown in the accompanying drawings shall be interpreted as illustrative and not in a limiting sense.

I claim:

1. A dental syringe tip for use with a hand-piece of an air-water syringe to deliver air and water to a mouth of patient, the syringe having air and water conduits for delivering air and water to a discharge end of the hand-piece, the dental syringe tip comprising a single unitary tube releasably engageable with the discharge end of the hand-piece, the tube having single a fluid passageway extending from an intake port at an intake end of the tube for fluid communication with the air and water conduits of the hand-piece and a discharge port at a discharge end of the tube for delivering at least one of the air and water through the passageway to the mouth of the patient, wherein the intake end of the tube is shaped and constructed to enable air and water flow through the air and water conduits when at least a portion of the intake end of the tube engages the discharge end of the hand-piece, and wherein the intake end of the tube at least partially defines a chamber when said portion of the intake end of the tube engages the discharge end of the hand-piece for transporting air from the air conduit of the hand-piece to the intake port of the tube and for transporting water from the water conduit of the hand-piece to the intake port of the tube.

2. A dental syringe tip for use with a hand-piece of an air-water syringe to deliver fluid to a mouth of patient, the syringe having a fluid conduit for delivering fluid to a discharge end of the hand-piece, the syringe tip comprising:

a tube releasably engageable with the discharge end of the hand-piece, the tube having an intake end and a discharge end;

a fluid passageway defined at least in part by the tube having an intake port adjacent the intake end of the tube for fluid communication with the fluid conduit of the hand-piece and a discharge port adjacent the discharge end of the tube for delivering the fluid to the mouth of the patient; and a viscous liquid occluding at least a portion of the fluid passageway for being dispensed through the discharge port into the mouth of the patient when fluid is delivered through the fluid passageway to the mouth of the patient, said liquid having a viscosity which is sufficiently great to resist leaking from the passageway before engaging the tube with the hand-piece and delivering fluid through the fluid passageway.

3. A syringe tip for use with a hand-piece of an air-water syringe to deliver air and water to a mouth of patient, the syringe having air and water conduits for delivering fluid to a discharge end of the hand-piece, the syringe tip comprising:

a single unitary tube releasably engageable with the discharge end of the hand-piece, the tube having an intake end and a discharge end;

a fluid passageway defined at least in part by the tube having an intake port adjacent the intake end of the tube for fluid communication with the air and water conduits of the hand-piece and a discharge port adjacent the discharge end of the tube for delivering fluid to the mouth of the patient;

a treating agent within the fluid passageway for being dispensed through the discharge port into the mouth of the patient when fluid is delivered through the fluid passageway to the mouth of the patient.

4. A syringe tip as set forth in claim 3 wherein said treating agent extends lengthwise along the tube.

5. A syringe tip as set forth in claim 4 wherein the treating agent comprises a water soluble substance.

6. A syringe tip as set forth in claim 5 wherein the treating agent comprises a water soluble foam.

7. A syringe tip as set forth in claim 3 further comprising a porous body positioned within the fluid passageway for retaining the treating agent until fluid passing through the tube washes the treating agent from the body and carries the treating agent out the discharge port of the tube.

8. A syringe tip as set forth in claim 7 wherein the tube has a rear portion, an intermediate portion and a forward portion, the rear portion extending forward from the intake end of the tube to the intermediate portion, the forward portion extending generally forward from the intermediate portion to the discharge end of the tube, and the intermediate portion has a bend.

9. A syringe tip as set forth in claim 8 wherein the porous body is positioned within the intermediate portion of the tube upstream from the bend.

* * * * *

UNITED STATES PATENT AND TRADEMARK OFFICE
CERTIFICATE OF CORRECTION

PATENT NO. : 6,113,391
DATED : September 5, 2000
INVENTOR(S) : Bernard S. Esrock It is certified that error appears in the above-identified patent and that said Letters Patent is hereby corrected as shown below:

<u>Title page,</u>
Item [75], Inventor's address reads "320Dungate Dr., Chesterfield, MO 63017" and should read -- 896 Bluespring Lane, Frontenac, MO 63131 --.

<u>Column 1,</u>
Line 5, line left out "BACKGROUND OF INVENTION."
Line 22, reads "cuter tube" and should read -- outer tube --.
Line 38, reads "simply" and should read -- simplify --.
Line 42, reads "to easier select" and should read -- to easily select --.
Line 49, reads "pre-measured" and should read -- premeasured --.

<u>Column 2,</u>
Line 9, reads "flow-na" and should read -- flowing --.
Line 34, reads "FIG. 3 is cross sectional" and should read -- FIG. 3 is a cross sectional --.

<u>Column 3,</u>
Line 11, reads "(air conduit for" and should read -- (air conduit) for --.
Line 21, reads "handle position 28" and should read -- handle portion 28 --.

<u>Column 4,</u>
Line 22, reads "preferably planar id and" and should read -- preferably planar and --.
Line 54, reads "ocher" and should read -- other --.
Line 55, reads "of least" and should read -- of at least --.
Line 60, reads "contain treating agent" and should read -- contain a treating agent --.
Line 63, reads "fluid Passageway 22" and should read -- fluid passageway 22 --.

<u>Column 5,</u>
Line 2, reads "MORGAN & BERRY®mouthwash" and should read -- MORGAN & BERRY® mouthwash --.
Line 25, reads "amount" and should read -- volume --.
Line 51, reads "syringe tip, 110" and should read -- syringe tip 110 --.

UNITED STATES PATENT AND TRADEMARK OFFICE
CERTIFICATE OF CORRECTION

PATENT NO.   : 6,113,391
DATED        : September 5, 2000
INVENTOR(S)  : Bernard S. Esrock It is certified that error appears in the above-identified patent and that said Letters Patent is hereby corrected as shown below:

Column 6,
Line 42, "mouth of patient" and should read -- mouth of a patient --.
Line 45, "having single a fluid" and should read -- having a single fluid --.

Column 7,
Line 24, reads "a fluid passageway" and should read -- a single fluid passageway --.
Line 24, reads "mouth of the patient;" and should read -- mouth of the patient; and --.

Signed and Sealed this

Thirty-first Day of December, 2002

JAMES E. ROGAN
*Director of the United States Patent and Trademark Office*